United States Patent
More et al.

(10) Patent No.: US 11,168,107 B2
(45) Date of Patent: Nov. 9, 2021

(54) AMINE SALT OF OBETICHOLIC ACID

(71) Applicant: DR. REDDY'S LABORATORIES LIMITED, Hyderabad (IN)

(72) Inventors: Satishbhai Sukhlalbhai More, Hyderabad (IN); Vikas Sadashiv Gajare, Hyderabad (IN); Sandip Ramdas Khobare, Hyderabad (IN); Krishna Mohan Thalabathula, Hyderabad (IN); Vilas Hareshwar Dahanukar, Hyderabad (IN); Shirshendu Das Gupta, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 642 days.

(21) Appl. No.: 16/077,947

(22) PCT Filed: Feb. 10, 2017

(86) PCT No.: PCT/IB2017/050728
§ 371 (c)(1),
(2) Date: Aug. 14, 2018

(87) PCT Pub. No.: WO2017/137931
PCT Pub. Date: Aug. 17, 2017

(65) Prior Publication Data
US 2021/0188896 A1 Jun. 24, 2021

(30) Foreign Application Priority Data

Feb. 10, 2016 (IN) .............................. 201641004703
Oct. 6, 2016 (IN) .............................. 201641034308

(51) Int. Cl.
*C07J 9/00* (2006.01)

(52) U.S. Cl.
CPC ........... *C07J 9/005* (2013.01); *C07B 2200/13* (2013.01)

(58) Field of Classification Search
CPC .............................. C07B 2200/13; C07J 9/005
See application file for complete search history.

(56) References Cited

U.S. PATENT DOCUMENTS

| 7,138,390 B2 | 11/2006 | Pellicciari |
| 2002/0120137 A1 | 8/2002 | Houze et al. |
| 2005/0080064 A1* | 4/2005 | Pellicciari ................ C07J 9/005 514/176 |

FOREIGN PATENT DOCUMENTS

WO 2013/192097 A1 12/2013

OTHER PUBLICATIONS

Berge, et al. Journal of Pharmaceutical Sciences, Jan. 1977, vol. 66, pp. 1-18.*
International Search Report dated Jun. 7, 2017, for corresponding International Patent Application No. PCT/IB2017/050728.
Written Opinion dated Jun. 7, 2017, for corresponding International Patent Application No. PCT/IB2017/050728.
International Preliminary Report on Patentability dated Aug. 14, 2018, for corresponding International Patent Application No. PCT/IB2017/050728.

* cited by examiner

*Primary Examiner* — Shawquia Jackson
(74) *Attorney, Agent, or Firm* — Pergament & Cepeda LLP; Milagros A. Cepeda; Edward D. Pergament

(57) ABSTRACT

The present application relates to amine salt of obeticholic acid. Specifically, the present application relates to (S)-α-methylbenzylamine and diethylamine salt of obeticholic acid. The present application also relates to a process for preparation of amorphous form of obeticholic acid comprising converting amine salt of obeticholic acid to amorphous form of obeticholic acid.

13 Claims, 1 Drawing Sheet

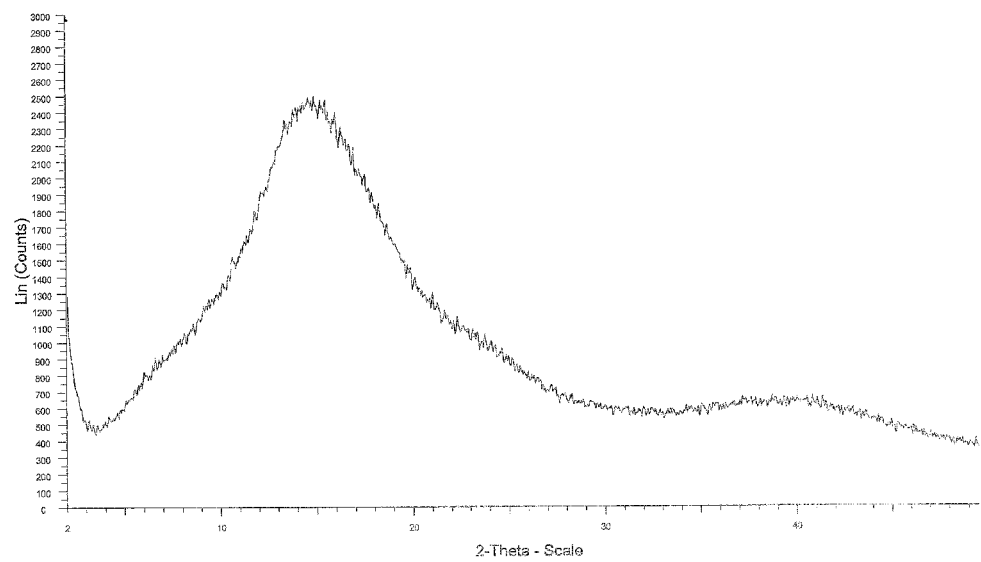

AMINE SALT OF OBETICHOLIC ACID

This application is a National Stage Application under 35 U.S.C. § 371 of PCT International Application No. PCT/IB2017/050728, filed Feb. 10, 2017, which takes priority from Indian Provisional Application Numbers IN 201641004703, filed Feb. 10, 2016; and IN 201641034308, filed Oct. 6, 2016, all of which are herein incorporated in their entireties.

INTRODUCTION

One aspect of the present application relates to amine salts of obeticholic acid and process for preparation thereof. Another aspect of the present application relates to process for preparation of amorphous form of obeticholic acid comprising converting amine salt of obeticholic acid to amorphous form of obeticholic acid.

Obeticholic acid is a semi-synthetic bile acid analogue. It is an agonist of farnesoid X receptor (FXR) ligand. Obeticholic acid is indicated for the treatment of primary biliary cirrhosis (PBC). PCT patent application, WO2002072598A1 (hereinafter referred as the WO'598 application) discloses obeticholic acid and process for preparation thereof. Obeticholic acid is chemically known as 6α-ethyl-chenodeoxycholic acid and has following structural formula:

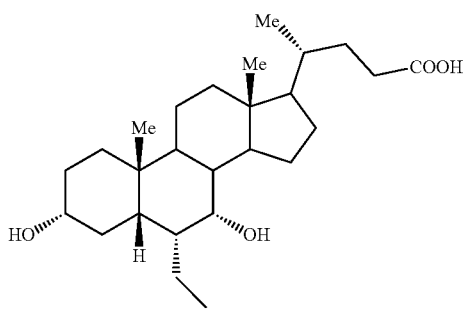 [SMILES: CC[C@H]1[C@@H](O)C2C3CCC([C@H](C)CCC(=O)O)[C@@]3(C)CCC2[C@@]2(C)CC[C@@H](O)C[C@@H]12]

PCT patent application, WO2013192097A1 (hereinafter referred as the WO'097 application) discloses a process for preparing pure amorphous form of obeticholic acid comprising the step of converting crystalline form C of obeticholic acid to pure amorphous form. Amorphous form has been designated as form 1 in the WO'097 application. PCT patent application, WO2002072598A1 (hereinafter referred as WO'598 application) discloses a process for preparing amorphous obeticholic acid comprising the step of converting a crystalline form of obeticholic to amorphous obeticholic acid Obeticholic acid is steroidal molecule and hence achieving ICH grade of purity is known to be difficult. Moreover, the starting material for the synthesis of obeticholic acid is chenodeoxycholic acid which is obtained from animal origin. Hence, the purification of obeticholic acid is essential for the use of it as drug substance. Hence, there remains a need for alternate process for the preparation pure obeticholic acid.

SUMMARY

One aspect of the present application relates to amine salt of obeticholic acid.

Another aspect of the present application relates to crystalline amine salt of obeticholic acid.

Yet another aspect of the present application relates to (S)-α-methylbenzylamine salt of obeticholic acid.

Still another aspect of the present application relates to diethylamine salt of obeticholic acid.

Another aspect of the present application relates to a process for the preparation of amine salt of obeticholic acid comprising:
  a) dissolving crude obeticholic acid in a suitable solvent or mixture thereof;
  b) optionally filtering the un-dissolved particles;
  c) adding an amine to the solution of step b);
  d) isolating amine salt of obeticholic acid form the solution of step c); and
  e) optionally, drying the isolated product at suitable temperature.

Still another aspect of the present application relates to a process for preparation of amorphous form of obeticholic acid comprising converting amine salt of obeticholic acid to amorphous form of obeticholic acid.

Yet another aspect of the present application relates to a process for preparation of amorphous form of obeticholic acid comprising converting (S)-α-methyl-benzylamine salt of obeticholic acid to amorphous form of obeticholic acid.

Another aspect of the present application relates to a process for preparation of amorphous form of obeticholic acid comprising converting amine salt of obeticholic acid to amorphous form of obeticholic acid.

BRIEF DESCRIPTION OF DRAWING

FIG. 1: The PXRD pattern of amorphous form of obeticholic acid obtained by the process of example 11.

DETAILED DESCRIPTION

One aspect of the present application relates to amine salt of obeticholic acid. Examples of useful amines which form amine salt of obeticholic acid include, but are not limited to, tert-butylamine, diethylamine, dibutylamine, morpholine, 3-dimethylamino-1-propylamine, dicyclohexylamine (DCHA), diisopropylamine, N-tert-butylbenzylamine, N-benzylmethylamine, (R)-α-methylbenzylamine, (S)-α-methylbenzylamine, benzylamine, dibenzylamine, cyclohexylamine and octylamine. Specifically, the amine may be selected from a group of (S)-α-methylbenzylamine and diethylamine. One specific aspect of the present application relates to (S)-α-methylbenzylamine salt of obeticholic acid. Another specific aspect of the present application relates to diethylamine salt of obeticholic acid.

It has now been found that an amine salt of obeticholic acid is generally a solid compound that can be easily purified by crystallization. Obeticholic acid obtained by using an amine salt of obeticholic acid as an intermediate is found to be more pure than obeticholic acid prepared directly, without using amine salts of obeticholic acid as an intermediate.

One aspect of the present application relates to a process for the preparation of amine salt of obeticholic acid comprising:
  a) dissolving crude obeticholic acid in a suitable solvent or mixture thereof;
  b) optionally filtering the un-dissolved particles;
  c) adding an amine to the solution of step b);
  d) isolating amine salt of obeticholic acid form the solution of step c); and e) optionally, drying the isolated product at suitable temperature.

In embodiments of step a), crude obeticholic acid may be dissolved in a suitable solvent or mixture thereof. The suitable solvents include, but not limited to, alcohols such as methanol, isopropanol and the like; ketones such as acetone, methyl isobutyl ketone and the like; ethers such as diethyl ether, tetrahydrofuran and the like; esters such as ethyl acetate, n-butyl acetate and the like; water and mixture thereof. In one embodiment, the solvent may be an alcohol solvent. Specifically, the alcohol solvent may be selected from a group of methanol and isopropanol. In another embodiment, the solvent may be a mixture of alcohol solvent and water. Specifically, the solvent may be selected from a group of methanol-water and isopropanol-water. In another embodiment, the solvent may be an ester solvent. Specifically, the ester solvent may be ethyl acetate. Crude obeticholic acid may be dissolved in a suitable solvent or mixture thereof at room temperature or by heating a suspension of obeticholic acid in a suitable solvent or mixture thereof at its boiling point. Specifically, crude obeticholic acid may be dissolved in a suitable solvent or mixture thereof at room temperature.

In embodiments of step b), the solution may be optionally filtered to remove any un-dissolved particles.

In embodiments of step c), the amine may be selected from a group of tert-butylamine, diethylamine, dibutylamine, morpholine, 3-dimethylamino-1-propylamine, dicyclohexylamine (DCHA), diisopropylamine, N-tert-butylbenzylamine, N-benzylmethylamine, (R)-α-methylbenzylamine, (S)-α-methylbenzylamine, benzylamine, dibenzylamine, cyclohexylamine and octylamine. Specifically, the amine may be selected from a group of (S)-α-methylbenzylamine and diethylamine. In one specific embodiment, the amine is (S)-α-methylbenzylamine. In another specific embodiment, the amine is diethylamine. The desired amine may be added to the solution of crude obeticholic acid in a suitable solvent or mixture thereof directly. In another embodiment, a solution containing the desired amine in a suitable solvent or mixture thereof may be added to the solution of crude obeticholic acid in a suitable solvent or mixture thereof. In yet another embodiment, the reverse addition may also be performed wherein the solution of crude obeticholic acid in a suitable solvent or mixture thereof may be added to the amine or a solution of amine in a suitable solvent or mixture thereof. The reaction mass containing the desired amine and crude obeticholic acid in a suitable solvent or mixture thereof may be stirred for a period sufficient to form the desired product at a temperature between about 0° C. to about the boiling point of the solvent. Specifically, the reaction mass may be stirred for about 5 minutes to about 2 hours at the boiling temperature of the solvent. More specifically, the reaction mass may be stirred for about 30 minutes to about 60 minutes at the boiling temperature of the solvent. In one embodiment, water may be added slowly to the reaction mass during heating at reflux temperature. In one embodiment, the amine salt of obeticholic acid may be added to the reaction mass as a seed material.

In embodiments of step d), the amine salt of obeticholic acid may be isolated from the reaction mass by any method known in the art. Specifically, the reaction mass may be cooled up to about 0° C. More specifically, the reaction mass may be cooled to room temperature. The precipitated solid may be isolated by filtration.

In embodiments of step e), the wet solid may be dried. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 30 minutes to about 24 hours, or longer.

Optionally, the amine salt of obeticholic acid, as obtained above, may be crystallized from a suitable solvent or mixture thereof. The suitable solvent includes but not limited to alcohols such as methanol, isopropanol and the like; ketones such as acetone, methyl isobutyl ketone and the like; chlorinated solvent such as chloroform, dichloromethane and the like; ethers such as diethyl ether, tetrahydrofuran and the like; esters such as ethyl acetate, n-butyl acetate and the like and mixture thereof. In one embodiment, the solvent may be an alcohol solvent. Specifically, the alcohol solvent may be isopropanol. In another embodiment, the solvent may be an ester solvent. Specifically, the ester solvent may be ethyl acetate. In another specific embodiment, the ester solvent may be n-butyl acetate. In one embodiment, the solvent may be an ether solvent. Specifically, the ether solvent may be methyl tert-butyl ether. In yet another embodiment, the solvent may be a ketone solvent. Specifically, the solvent may be acetone. In still another embodiment, the solvent may be a chlorinated solvent. Specifically, the solvent may be dichloromethane.

Amine salt of obeticholic acid may be dissolved in the suitable solvent or mixture thereof at a temperature from about 0° C. to about boiling point of the solvent. Specifically, amine salt of obeticholic acid may be dissolved in the suitable solvent or mixture thereof at a temperature from about room temperature to about boiling point of the solvent. The reaction mass containing the amine salt of obeticholic acid and a suitable solvent or mixture thereof may be stirred for a sufficient time at a temperature between about 0° C. to about the boiling point of the solvent Specifically, the reaction mass containing the amine salt of obeticholic acid and a suitable solvent or mixture thereof may be stirred for about 5 minutes to about 2 hours at the boiling temperature of the solvent. More specifically, the reaction mass containing the amine salt of obeticholic acid and a suitable solvent or mixture thereof may be stirred for about 30 minutes to about 60 minutes at the boiling temperature of the solvent. The amine salt of obeticholic acid may be precipitated from the reaction mass either by cooling the reaction mass or by adding an anti-solvent to the reaction mass. The anti-solvent may include but not limited to hydrocarbon solvents like heptanes, hexanes and the like; aromatic hydrocarbon solvents like toluene, xylene and the like or mixture thereof.

Specifically, the reaction mass containing the amine salt of obeticholic acid and a suitable solvent or mixture thereof may be cooled up to about 0° C. Specifically, the reaction mass containing the amine salt of obeticholic acid and a suitable solvent or mixture thereof may be cooled to about room temperature. The precipitated solid may be isolated by any method known in the art. Specifically, the precipitated solid may be isolated by filtration. Optionally, the wet solid may be dried. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 30 minutes to about 24 hours, or longer.

Another aspect of the present application relates to a process for preparation of amorphous form of obeticholic acid comprising converting amine salt of obeticholic acid to amorphous form of obeticholic acid. In one embodiment, the amines which form amine salt of obeticholic acid include, but are not limited to, tert-butylamine, diethylamine, dibutylamine, morpholine, 3-dimethylamino-1-propylamine, dicyclohexylamine (DOHA), diisopropylamine, N-tert-butylbenzylamine, N-benzylmethylamine, (R)-α-methylbenzylamine, (S)-α-methylbenzylamine, benzylamine, dibenzylamine, cyclohexylamine and octylamine. In one specific embodiment, the present application relates to a process for preparation of amorphous form of obeticholic acid comprising converting (S)-α-methylbenzylamine salt of obeticholic acid to amorphous form of obeticholic acid. In another specific embodiment, the present application relates to a process for preparation of amorphous form of obeticholic acid comprising converting diethylamine salt of obeticholic acid to amorphous form of obeticholic acid.

The amine salt of obeticholic acid may be dissolved in a suitable solvent or mixture thereof. The suitable solvent includes but not limited to alcohols such as methanol, isopropanol and the like; ketones such as acetone, methyl isobutyl ketone and the like; ethers such as diethyl ether, tetrahydrofuran and the like; esters such as ethyl acetate, n-butyl acetate and the like; water and mixture thereof. Specifically, the suitable solvent may be water. In one embodiment, an aqueous solution of a suitable base may be added to the solution containing amine salt of obeticholic acid. The reverse mode of addition may also be performed wherein the amine salt of obeticholic acid may be added to the aqueous solution of the suitable base directly, or a solution containing amine salt of obeticholic acid in a suitable solvent may be added to the aqueous solution of the suitable base. Specifically, amine salt of obeticholic acid may be added directly to the aqueous solution of the suitable base.

The suitable base includes but not limited to hydroxides such as sodium hydroxide, potassium hydroxide and the like; carbonates such as sodium carbonate, potassium carbonate and the like; bicarbonates such as sodium bicarbonate, potassium bicarbonate and the like; organic base like triethylamine and the like. Specifically, the base may be sodium hydroxide. The reaction mass containing an aqueous solution of the suitable base and amine salt of obeticholic acid may be washed with an organic solvent. The organic solvent includes but not limited to ethers such as methyl tert-butyl ether, diethyl ether and the like; hydrocarbons such as hexanes, heptanes and the like; aromatic hydrocarbons such as toluene, xylene and the like; ester solvent such as ethyl acetate, isopropyl acetate and the like or mixture thereof. The organic solvent may be removed by decantation and the remaining aqueous solution may be acidified by a suitable acid including but not limited to mineral acid such as hydrochloric acid, hydrobromic acid and the like; organic acid such as oxalic acid, tartaric acid and the like. Specifically, the remaining aqueous solution may be acidified by hydrochloric acid. The precipitated solid may be isolated by any method known in the art.

In another embodiment, an aqueous solution of amine salt of obeticholic acid may be added to an aqueous solution of an acid including but not limited to mineral acid such as hydrochloric acid, hydrobromic acid and the like; organic acid such as oxalic acid, tartaric acid and the like. In yet another embodiment, an aqueous solution of an acid may be added to an aqueous solution of amine salt of obeticholic acid. Specifically, an aqueous solution of amine salt of obeticholic acid may be added to an aqueous solution of hydrochloric acid. The precipitated solid may be isolated by any method known in the art.

Specifically, the precipitated solid may be isolated by filtration. Optionally, the wet solid may be dried. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 30 minutes to about 24 hours, or longer.

Definitions

The following definitions are used in connection with the present application unless the context indicates otherwise.

The terms "about," "general, 'generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "room temperature" is taken to mean a temperature of about 20° C. to about 30° C.

The term "optional" or "optionally" is taken to mean that the event or circumstance described in the specification may or may not occur, and that the description includes instances where the event occurs and instances where it does not.

The term "Crude" is taken to mean that the material is not pure enough to be used as drug substance.

Certain specific aspects and embodiments of the present application will be explained in greater detail with reference to the following examples, which are provided only for purposes of illustration and should not be construed as limiting the scope of the disclosure in any manner.

EXAMPLES

Example 1: Preparation of (S)-α-Methylbenzylamine Salt of Obeticholic Acid

Crude obeticholic acid (2.0 g, Purity by HPLC: 97.49%) was dissolved in isopropanol (30 mL). To the above solution, (S)-α-methylbenzylamine (0.53 g) was added. The reaction mass was heated to reflux at about 80° C. to 84° C.

for about 30 to 60 minutes. The reaction mass was cooled to 25° C. to 35° C. and stirred for 1-2 hours. The precipitated solid was filtered and washed with isopropanol (10 mL). The solid was suck-dried and transferred into a separate reaction vessel containing isopropanol (11.25 mL). The reaction mass was heated to reflux at about 80° C. to 84° C. for about 30 to 60 minutes. The reaction mass was cooled to 25° C. to 35° C. and stirred for 1 hour. The precipitated solid was filtered and washed with isopropanol (3.0 mL). The wet solid was dried under vacuum at 50° C. for 4 to 6 hours to provide the title compound.
Yield: 69.8%
Purity (by HPLC): 99.24%

Example 2: Preparation of (S)-α-Methylbenzylamine Salt of Obeticholic Acid

Obeticholic acid (2.0 g, Purity by HPLC: 99.85%) was dissolved in methanol (20 mL) and added 20.0 mg (1% w/w) chenodeoxycholic acid (CDCA). To the above solution, (S)-α-methylbenzylamine (0.59 g) was added. The reaction mass was heated to reflux at about 61° C. to 67° C. for about 30 to 60 minutes. Water (20 mL) was added to the reaction mass at reflux temperature slowly. The reaction mass was refluxed further for about 15 to 45 minutes. The reaction mass was cooled to 25° C. to 35° C. and stirred for 30 to 60 minutes. The precipitated solid was filtered and washed with methanol-water (1:1; 6 mL). The solid was dried in an oven at 50° C. under vacuum for 2 hours to 6 hours to provide the desired compound.
Yield: 78.2%
Purity (by HPLC): 99.48% (CDCA Content: 0.40%)

Example 3: Preparation of (S)-α-Methylbenzylamine Salt of Obeticholic Acid

Obeticholic acid (2.0 g, Purity by HPLC: 99.85%) was dissolved in isopropanol (20 mL) and added 20.0 mg (1% w/w) chenodeoxycholic acid (CDCA). To the above solution, (S)-α-methylbenzylamine (0.59 g) was added. The reaction mass was heated to reflux at about 79° C. to 85° C. for about 30 to 60 minutes. Water (40 mL) was added to the reaction mass at reflux temperature slowly. The reaction mass was refluxed further for about 15 to 45 minutes. The reaction mass was cooled to 25° C. to 35° C. and stirred for 30 to 60 minutes. The precipitated solid was filtered and washed with isopropanol-water (1:2; 6 mL). The solid was dried in an oven at 50° C. under vacuum for 2 hours to 6 hours to provide the desired compound.
Yield: 60.7%
Purity (by HPLC): 99.57% (CDCA Content: 0.26%)

Example 4: Preparation of Amorphous Form of Obeticholic Acid

To a solution of sodium hydroxide (0.1 g) in water (6 mL), (S)-α-methylbenzylamine salt of obeticholic acid (1.2 g, Purity by HPLC: 99.24%) was added and stirred for 5-10 minutes. The aqueous solution was washed with methyl tert-butyl ether (MTBE) (3×6 mL) and the organic layer was removed. The traces of MTBE were removed by applying vacuum to aqueous layer for 5 to 10 minute. The aqueous reaction mass was filtered through charcoal pad and the charcoal pad was washed with water (0.3 mL). Concentrated hydrochloric acid (0.36 mL) was added to the aqueous reaction mass and the reaction temperature was raised to 30-35° C. The reaction mass was stirred for 30 minutes and allowed to cooled to 15-20° C. The reaction mass was stirred for 30-90 minutes at this temperature and the precipitated solid was filtered. The solid was dried at 45 to 50° C. in vacuum oven for 8-10 hours.
Yield: 90.6%
Purity (by HPLC): 99.15%

Example 5: Preparation of Diethylamine Salt of Obeticholic Acid

Obeticholic acid (1.0 g) was dissolved in ethyl acetate (10 mL) and stirred for 5 minutes. The reaction mass was slowly heated to 65-70° C. and a solution of diethylamine (0.174 g) in ethyl acetate (5 mL) was added. The reaction mass was cooled to 25° C. to 35° C. and stirred for 1-2 hours. The precipitated solid was filtered and washed with ethyl acetate (2 mL). The wet solid was dried under vacuum to provide the title compound.
Yield: 0.75 g
Purity (by HPLC): 99.84%

Example 6: Preparation of Amorphous Obeticholic Acid

Crude obeticholic acid (1.0 g, HPLC Purity: 95.7%) was dissolved in ethyl acetate (15 mL) and stirred for 5 minutes. The reaction mixture was slowly heated to 60-65° C. Diethylamine (0.174 g) was added to the above solution and stirred for 15-20 minutes. The reaction mass was cooled to 35° C. and again heated up to 60-65° C. The reaction mass was stirred for 15 minutes and seeded with diethylamine salt of obeticholic acid. The reaction mass was cooled to 30° C. and stirred for 45 minutes. The precipitated solid was filtered and washed with ethyl acetate (2 mL). The wet solid was dried under vacuum at to 50° C. to provide diethylamine salt of obeticholic acid (0.80 g).

The diethylamine salt of obeticholic acid, as prepared above, was mixed with aqueous solution of sodium hydroxide (0.19 g in 10 mL water). Ethyl acetate (10 mL) was added to the reaction mass and stirred for 20 minutes. The aqueous solution was separated and washed with ethyl acetate (10 mL). The aqueous layer was separated and the pH was made acidic by the addition of concentrated hydrochloric acid (0.21 g). The desired compound was extracted with ethyl acetate (2×10 mL). The combined organic layer was evaporated to provide the title compound.
Yield: 0.65 g
Purity (by HPLC): 97.50%

Example 7: Preparation of Diethylamine Salt of Obeticholic Acid

Crude obeticholic acid (5.5 g, 95.7%) and diethylamine (1.15 g) was mixed with ethyl acetate (55 mL) and the reaction mass was heated up to 70-80° C. for 2 hours. The reaction mass was cooled to 50-55° C. The reaction mass was concentrated under vacuum to provide the crude title compound as solid.
Yield: 5.92 g
Purity (by HPLC): 89.45%

Example 8: Preparation of Pure Diethylamine Salt of Obeticholic Acid

Example 8a: Preparation of Pure Diethylamine Salt of Obeticholic Acid by Crystallization Using Ethyl Acetate Crude diethylamine salt of obeticholic acid (0.5 g), as prepared in Example 7, was mixed with ethyl acetate (5 mL)

and heated to reflux at 70-80° C. for 10-15 minutes. The reaction mass was cooled to 27° C. gradually, filtered and washed with ethyl acetate (1 mL). The solid was dried under vacuum at 50° C. to provide the title compound.

Yield: 0.3 g
Purity (by HPLC): 97.70%

Example 8b: Preparation of Pure Diethylamine Salt of Obeticholic Acid by Crystallization Using Methyl Tert-Butyl Ether Crude diethylamine salt of obeticholic acid (0.5 g), as prepared in Example 7, was mixed with methyl tert-butyl ether (6 mL) and heated to reflux at 55° C. for 10 minutes. The reaction mass was cooled to 27° C. gradually, filtered and washed with methyl tert-butyl ether (2 mL). The solid was dried under vacuum at 50° C. to provide the title compound.

Yield: 0.35 g
Purity (by HPLC): 97.25%

Example 8c: Preparation of Pure Diethylamine Salt of Obeticholic Acid by Crystallization Using Acetone Crude diethylamine salt of obeticholic acid (0.5 g), as prepared in Example 7, was mixed with acetone (5 mL) and heated to reflux at 55° C. for 10 minutes. The reaction mass was cooled to 27° C. gradually, filtered and washed with acetone (0.5 mL). The solid was dried under vacuum at 50° C. to provide the title compound.

Yield: 0.33 g
Purity (by HPLC): 98.21%

Example 8d: Preparation of Pure Diethylamine Salt of Obeticholic Acid by Crystallization Using n-Butyl Acetate Crude diethylamine salt of obeticholic acid (0.5 g), as prepared in Example 7, was mixed with n-butyl acetate (5 mL) and heated to reflux at 80-90° C. for 10 minutes. The reaction mass was cooled to 27° C. gradually, filtered and washed with n-butyl acetate (0.5 mL). The solid was dried under vacuum at 50° C. to provide the title compound.

Yield: 0.35 g
Purity (by HPLC): 98.23%

Example 8e: Preparation of Pure Diethylamine Salt of Obeticholic Acid by Crystallization Using Dichloromethane Crude diethylamine salt of obeticholic acid (0.5 g), as prepared in Example 7, was mixed with dichloromethane (10 mL) and heated to reflux at 35-40° C. for 10 minutes. The reaction mass was cooled to 0-5° C. gradually, filtered and washed with dichloromethane (0.5 mL). The solid was dried under vacuum at 50° C. to provide the title compound.

Yield: 0.20 g
Purity (by HPLC): 98.22%

Example 8f: Preparation of Pure Diethylamine Salt of Obeticholic Acid by Crystallization Using n-Butyl Acetate Crude diethylamine salt of obeticholic acid (5.5 g, HPLC purity: 95.72%) was mixed with n-butyl acetate (27.5 mL) and heated to reflux at 70-85° C. for 15 minutes. Another lot of n-butyl acetate (27.5 mL) was added to the reaction mass. The reaction mass was cooled to 27° C. gradually, filtered and washed with n-butyl acetate (5.5 mL). The solid was dried under vacuum below 55° C. to provide the title compound.

Yield: 5.0 g
Purity (by HPLC): 98.15%

Example 9: Preparation of Pure Diethylamine Salt of Obeticholic Acid

Crude diethylamine salt of obeticholic acid (20.5 g, HPLC purity: 97.57%) was dissolved in ethyl acetate (200 mL) and heated up to about 78° C. Diethylamine (3.68 g) was added slowly to the above solution and stirred for 20 minutes. The reaction mass was gradually cooled to 25-35° C. The reaction mass was heated again to about 78° C. stirred at the temperature for 20 minutes. The reaction mass was again gradually cooled to 25-35° C. The precipitated solid was filtered and washed with ethyl acetate (40 mL).

The above obtained wet solid compound was mixed with n-butyl acetate (100 mL) and heated to about 88° C. The reaction mass was allowed to gradually cool to 25-35° C. The precipitated solid was filtered and washed with n-butyl acetate (40 mL). The solid was dried under vacuum below 50° C. for about 90 minutes to afford the title compound.

Yield: 17.1 g
Purity (by HPLC): 99.85%

Example 10: Preparation of Pure Diethylamine Salt of Obeticholic Acid

Crude diethylamine salt of obeticholic acid (28.4 g, HPLC purity: 94.31%) was dissolved in ethyl acetate (300 mL). Diethylamine (5.52 g) was added slowly to the above solution and heated to reflux at about 77° C. The reaction mass was gradually cooled to 53° C. and diethyalmine salt of obeticholic acid (0.075 g) was added to the reaction mass as a seed. The reaction mass further cooled to 28° C. and the precipitated solid was filtered and washed with ethyl acetate (60 mL).

The above obtained wet solid compound was mixed with n-butyl acetate (150 mL) and heated to about 80° C. The reaction mass was stirred at that temperature for 5 minutes and the reaction mass was allowed to gradually cool to 30° C. The precipitated solid was filtered and washed with n-butyl acetate (60 mL).

The wet solid, as obtained above, was mixed with n-butyl acetate (150 mL) and heated to about 80° C. The reaction mass was stirred at that temperature for 5 minutes and the reaction mass was allowed to gradually cool to 30° C. The precipitated solid was filtered and washed with n-butyl acetate (60 mL). The solid was dried under vacuum below 50° C.

The solid, as obtained above, was mixed with n-butyl acetate (150 mL) and heated to about 80° C. The reaction mass was stirred at that temperature for 5 minutes and the reaction mass was allowed to gradually cool to 30° C. The precipitated solid was filtered and washed with n-butyl acetate (60 mL). The solid was dried under vacuum below 50° C. to afford the title compound.

Yield: 20.6 g
Purity (by HPLC): 99.99%

Example 11: Preparation of Amorphous Obeticholic Acid

Diethyalime salt of obeticholic acid (10 g), as prepared in Example 9, was dissolved in water (100 mL). The above solution was added to a solution comprising water (120 mL) and concentrated hydrochloric acid (4.2 g, 35%) was added to the mixture. The reaction mass was stirred for about 2 hours and precipitated solid was filtered and washed with water (50 mL). The solid was dried under vacuum below 50° C. for about 7 hours to afford solid (7.75 g).

The solid (5.7 g) was mixed with micron-filtered water (150 mL) and the reaction mass was stirred for about 25-35° C. for about 14 hours. The solid was filtered and washed with water (2×37.5 mL) to afford the title compound.

Yield: 5.61 g
Purity (by HPLC): 99.93%

Example 12: Preparation of Amorphous Obeticholic Acid

Diethyalime salt of obeticholic acid (17 g), as prepared in Example 10, was dissolved in water (204 mL). The above solution was filtered through the micron-filter and the micron-filter was washed with water (34 mL). The above solution was added to a solution comprising water (204 mL) and concentrated hydrochloric acid (7.2 g, 35%) was added to the mixture. The reaction mass was stirred for about 1 hour at 25-35° C. and cooled to 15-20° C. The precipitated solid was filtered and washed with water (4×85 mL). The solid was mixed with water (340 mL) and stirred for 3 hours at 25-35° C. The solid was filtered and washed with water (2×85 mL). The solid was dried under vacuum at 50-55° C. for about 5 hours and 30 minutes to afford the desired product.

Yield: 12.3 g
Purity (by HPLC): 99.93%

We claim:

1. An amine salt of obeticholic acid, wherein the amine is (S)-α-methylbenzylamine.

2. A process for the preparation of amine salt of obeticholic acid comprising:
   a) dissolving crude obeticholic acid in a suitable solvent or mixture thereof;
   b) optionally filtering the un-dissolved particles;
   c) adding an amine to the solution of step b);
   d) isolating amine salt of obeticholic acid form the solution of step c); and
   e) optionally, drying the isolated product at suitable temperature.

3. The process of claim 2, wherein the amine in step c) is selected from a group of tert-butylamine, diethylamine, dibutylamine, morpholine, 3-dimethylamino-1-propylamine, dicyclohexylamine (DCHA), diisopropylamine, N-tert-butylbenzylamine, N-benzylmethylamine, (R)-α-methylbenzylamine, (S)-α-methylbenzylamine, benzylamine, dibenzylamine, cyclohexylamine and octylamine.

4. The process of claim 2, wherein the amine in step c) is selected from a group of (S)-α-methylbenzylamine and diethylamine.

5. The process of claim 2, wherein the amine is step c) is diethylamine.

6. The process of claim 2, wherein amine salt of obeticholic acid is crystallized from a suitable solvent selected from a group of alcohol solvent, ester solvent and ketone solvent.

7. The process of claim 2, wherein amine salt of obeticholic acid is crystallized from n-butyl acetate.

8. The process of claim 2, wherein amine salt of obeticholic acid is crystallized from acetone.

9. The process of claim 2, wherein amine salt of obeticholic acid is crystallized from isopropanol.

10. A process for preparation of amorphous form of obeticholic acid comprising converting amine salt of obeticholic acid to amorphous form of obeticholic acid.

11. The process of claim 9, wherein the amine salt is (S)-α-methylbenzylamine salt of obeticholic acid.

12. The process of claim 9, wherein the amine salt is diethylamine salt of obeticholic acid.

13. The process of claim 9, comprising the step of addition of an aqueous solution comprising amine salt of obeticholic acid to an aqueous solution of an acid.

\* \* \* \* \*